United States Patent [19]
Hittich et al.

[11] Patent Number: 5,565,140
[45] Date of Patent: Oct. 15, 1996

[54] HALOGENATED BENZENE DERIVATIVES, AND A LIQUID-CRYSTALLINE MEDIUM

[75] Inventors: Reinhard Hittich, Modautal; Eike Poetsch, Mühltal; Volker Reiffenrath, Rossdorf; Bernhard Rieger, Münster-Altheim; Andreas Wachtler, Griesheim, all of Germany; David Coates, Merley, Great Britain; Herbert Plach, Darmstadt, Germany

[73] Assignee: Merck Patent Gesellschaft Mit Beschrankter Haftung, Darmstadt, Germany

[21] Appl. No.: 461,740

[22] Filed: Jun. 5, 1995

Related U.S. Application Data

[63] Continuation of Ser. No. 197,987, Apr. 4, 1994, abandoned, which is a continuation of Ser. No. 623,380, Nov. 15, 1990, Pat. No. 5,308,541.

[30] Foreign Application Priority Data

| | | | |
|---|---|---|---|
| Aug. 30, 1989 | [DE] | Germany | 39 28 656.8 |
| Aug. 30, 1989 | [DE] | Germany | 39 28 657.6 |
| Jan. 22, 1990 | [GB] | United Kingdom | 9001408 |
| Mar. 28, 1990 | [DE] | Germany | 40 09 928.8 |

[51] Int. Cl.[6] .......................... C09K 19/30; C09K 19/12; G02F 1/13; C07C 25/00
[52] U.S. Cl. .................... 252/299.63; 252/299.01; 252/299.66; 359/103; 570/127; 570/130; 570/131
[58] Field of Search .................... 252/299.01, 299.63, 252/299.66; 570/127, 130, 131; 359/103

[56] References Cited

U.S. PATENT DOCUMENTS

| | | |
|---|---|---|
| 4,439,340 | 3/1984 | Kojima et al. .................... 252/299.63 |
| 4,652,089 | 3/1987 | Oesterhelt et al. . |
| 4,659,502 | 4/1987 | Feron et al. . |
| 4,797,228 | 1/1989 | Goto et al. . |
| 4,814,523 | 10/1989 | Tanaka et al. . |
| 4,820,443 | 4/1989 | Goto et al. . |
| 4,871,469 | 7/1991 | Goto et al. . |
| 5,032,313 | 7/1991 | Goto et al. . |
| 5,064,567 | 11/1991 | Fanada et al. . |
| 5,122,295 | 6/1992 | Weber et al. . |
| 5,286,411 | 2/1994 | Reiger et al. .................... 252/299.63 |
| 5,308,541 | 5/1994 | Hittich et al. . |
| 5,350,535 | 9/1994 | Reiger et al. .................... 252/299.63 |
| 5,368,772 | 11/1994 | Reiger et al. .................... 252/299.63 |

FOREIGN PATENT DOCUMENTS

| | | |
|---|---|---|
| 272580 | 6/1981 | European Pat. Off. . |
| 2-6636 | 2/1988 | European Pat. Off. . |
| 2193209 | 2/1988 | United Kingdom . |

*Primary Examiner*—Shean C. Wu
*Attorney, Agent, or Firm*—Millen, White, Zelano & Branigan, P.C.

[57] ABSTRACT

The invention relates to novel halogenated benzene derivatives of the formula I

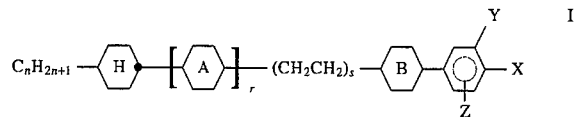

in which n is 1 to 7 [sic], the rings A and B are each trans-1,4-cyclohexylene, or one of the rings A and B is alternatively 1,4-phenylene or 3-fluoro-1,4-phenylene, X is F, Cl, $CHF_2$, $-CF_3$, $-CN$, $-OCF_3$ or $-OCHF_2$, Y and Z are each, independently of one another, H or F, r=1 or, in the case where s=1, B=trans-1,4-cyclohexylene and simultaneously X=$-CHF_2$, $-CF_3$, $-OCF_3$ or $-OCHF_2$, r is alternatively 0, and s=1 or, in the case where B=1,4-phenylene or 3-fluoro-1,4-phenylene, s=0.

16 Claims, No Drawings

HALOGENATED BENZENE DERIVATIVES, AND A LIQUID-CRYSTALLINE MEDIUM

This is a continuation of the application Ser. No. 08/197,987 filed Apr. 4, 1994, now abandoned, which is a continuation of Ser. No. 07/623,380 filed Nov. 15, 1990 now U.S. Pat. No. 5,308,541.

The invention relates to novel halogenated benzene derivatives of the formula I

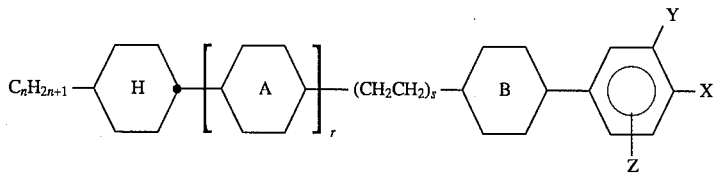

in which n is 1 to 10, the rings A and B are each trans-1,4-cyclohexylene, or one of the rings A and B is alternatively 1,4-phenylene or 3-fluoro-1,4-phenylene, X is F, Cl, —$CHF_2$, —$CF_3$, —CN, —$OCF_3$ or —$OCHF_2$, Y and Z are each, independently of one another, H or F, r=1 or, in the case where s=1, B=trans-1,4-cyclohexylene and simultaneously X=—$CHF_2$, —$CF_3$, —$OCF_3$ or —$OCHF_2$, r is alternatively 0, and s=1 or, in the case where B=1,4-phenylene or 3-fluoro-1,4-phenylene, s is alternatively 0, and liquid-crystalline media containing these compounds.

DESCRIPTION OF THE ART

EP-A 0 205 998 and 0 291 949 disclose liquid crystals of the formula A1

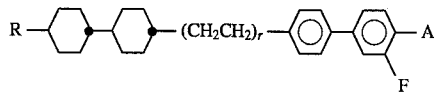

in which A is F or CN, and R is alkyl having 1 to 7 carbon atoms.

However, the compounds where A=F have only moderate dielectric anisotropy, which frequently results in relatively high threshold voltages in mixtures.

In addition, the miscibility of the compounds A1 with other liquid-crystal compounds is in some cases inadequate.

Further, similar nitrile compounds are known:

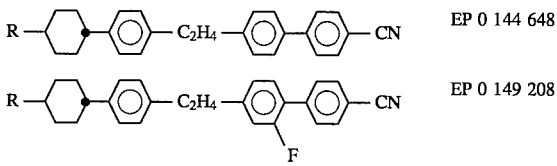

EP-A 0 280 902 discloses liquid crystals of the formula A2

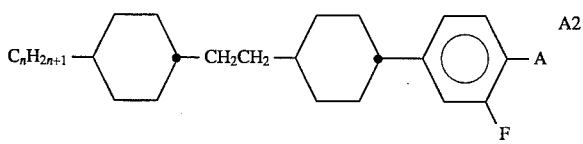

in which A is H, F, Cl, Br or CN.

EP-A 0 272 580 discloses liquid crystals of the formula B

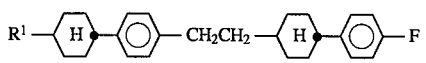

in which $R^1$ is $C_2H_5$ or $C_4H_7$.

However, the compounds A2 are either not up to the high demands regarding electrical resistance (A=CN), as required, for example, for displays having an active matrix, or they have only moderate dielectric anisotropy, which frequently results in relatively high threshold voltages in mixtures (A=H, F, Cl or Br). By contrast, the compounds B have extremely high melting points and relatively unfavorable miscibility with other liquid-crystal compounds. In addition, their dielectric anisotropy is extremely low.

Like similar compounds, for example those disclosed in German Offenlegungsschrift 33 17 597, the compounds of the formula I can be used as components of liquid-crystalline media, in particular for displays based on the principle of the twisted cell.

All the substances employed hitherto for this purpose have certain disadvantages, for example excessively high melting points, excessively low clear points, inadequate stability to heat, light or electrical fields, inadequate electrical resistance, excessive temperature dependence of the threshold voltage, induction of smectic phases at low temperatures and/or inadequate solubility at low temperatures.

In particular in the case of displays of the supertwist type (STN) having twist angles of considerably more than 220° or in the case of displays having an active matrix, the materials employed hitherto have disadvantages.

SUMMARY OF THE INVENTION

The invention had the object of finding novel liquid-crystalline compounds which are suitable as components of liquid-crystalline media, in particular for nematic media having positive dielectric anisotropy, and which do not have the disadvantages of the known compounds, or only do so to a small extent. This object has been achieved by the provision of the novel compounds of the formula I.

It has been found that the compounds of the formula I are pre-eminently suitable as components of liquid-crystalline media. They can be used, in particular, to obtain liquid-crystalline media having broad nematic ranges, high clear point, excellent nematogeneity down to low temperatures, excellent chemical stability, a pronounced ε⊥ with a positive dielectric anisotropy, low temperature dependence of the threshold voltage and/or low optical anisotropy. The novel compounds also exhibit good solubility for or in other components of media of this type and a high positive dielectric anisotropy at the same time as favorable viscosity.

DESCRIPTION OF THE PREFERRED EMBODIMENTS

The nitriles of the formula I (X=CN) [in particular those of the formulae Iaa (s is preferably 1), Iac, Ib, Ibd (Y is preferably F), Ibf and Ibg] exhibit, for high-clearing compounds, very good solubilities in many standard base mixtures at the same time as low viscosity and high nematogeneity. They are particularly suitable as high-clearing compounds for TN and STN mixtures or for PDLC applications (PDLC/NCAP or PN) due to the favorable values for the birefringence. The nitriles (in particular of the formula Iaa) have very good stability to visible and UV light. The nitriles of the formula Iaa are highly suitable for nematic broad-range mixtures and, in particular in combination with nematic materials of relatively high birefringence, have only a low tendency toward formation of smectic phases at low temperatures. The particularly low temperature dependence of the threshold voltage of such mixtures should also be emphasized. The higher homologs are preeminently suitable for $S_A$ O mixtures.

The compounds of the formula I facilitate both STN displays having a very steep electro-optical characteristic line and displays having an active matrix which have excellent long-term stability.

In the pure state, the compounds of the formula I are colourless and form liquid-crystalline mesophases in a temperature range which is favorably located for electro-optical use.

The invention thus relates to the compounds of the formula I and to the use of the compounds of the formula I as components of liquid-crystalline media, to liquid-crystalline media containing at least one compound of the formula I, and to electro,optical displays which contain media of this type.

Above and below, n, r, s, A, B, X, Y and Z are as defined, unless expressly stated otherwise.

In the compounds of the formula I, the alkyl groups $C_nH_{2n+1}$ are preferably straight-chain. Accordingly, $C_nH_{2n+1}$ is preferably methyl, ethyl, n-propyl, n-butyl, n-pentyl, n-hexyl or n-heptyl. n is preferably 1 to 7, particularly 2, 3, 4 or 5.

Compounds of the formula I containing branched alkyl groups may occasionally be important due to better solubility in the customary liquid-crystalline base materials, but in particular as chiral dopes, if they are optically active. Branched groups of this type generally contain not more than one chain branch. Preferred branched alkyl radicals are isopropyl, 2-butyl (=1-methylpropyl), isobutyl (=2-methylpropyl), 2-methylbutyl, isopentyl (=3-methylbutyl), 2-methylpentyl, 3-methylpentyl or 2-heptyl (=1-methylhexyl).

The radical

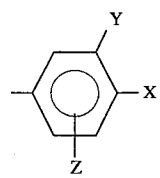

is preferably

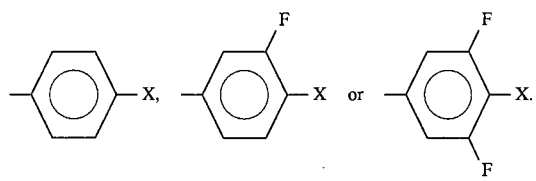

X is preferably F, Cl, —$CF_3$, —$OCHF_2$ or —$OCF_3$.

Particular preference is given to the compounds of the formula I with the proviso that (a) in the case where r=s=1, A=1,4-phenylene, B=trans-1,4-cyclohexylene and at the same time X=F or Cl Y and/or Z is fluorine, and (b) in the case where r=1, A=trans-1,4-cyclohexylene and at the same time X =F, B is 3-fluoro-1,4-phenylene or trans-1,4-cyclohexylene and/or Y and Z are each fluorine.

Particular preference is given to the compounds of the following sub-formulae:

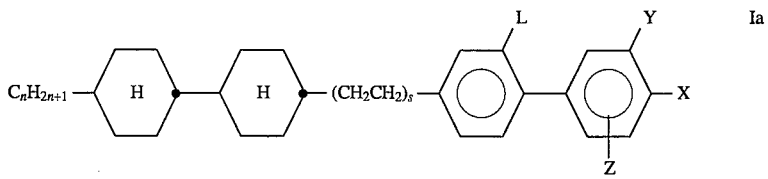

Ia in which n is 1 to 7, s is 0 or 1, X is F, Cl, —$CHF_2$, —$CF_3$, —$OCF_3$ or —$OCHF_2$, and Y, L and Z are each, independently of one another, H or F, with the proviso that, in the case where X=F, L=F, L=Y=F or Y=Z=F.

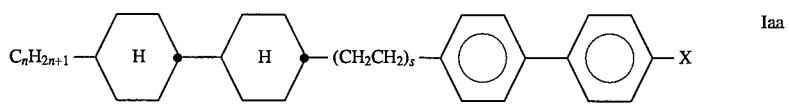

Iaa in which X is Cl, —CN, —$CF_3$, —$CHF_2$, —$OCF_3$ or —$OCHF_2$.

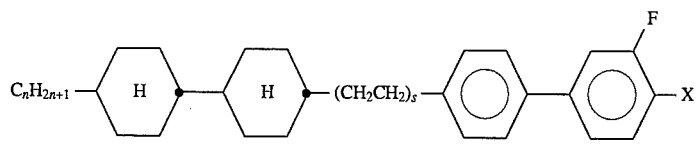

in which X is Cl, —CF$_3$, —CHF$_2$, —OCF$_3$ or —OCHF$_2$.

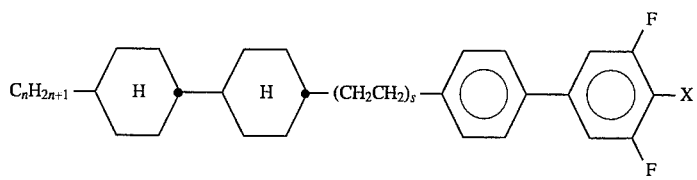

in which X is F, Cl, —CF$_3$, —CHF$_2$, —OCF$_3$ or —OCHF$_2$.

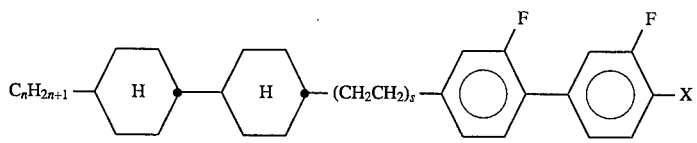

in which X is F, Cl, —CF$_3$, —CHF$_2$, —OCF$_3$ or —OCHF$_2$,

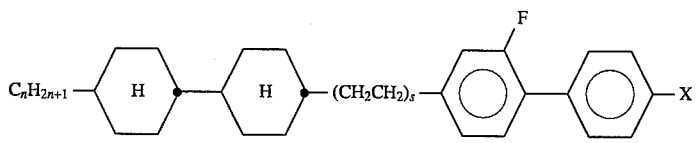

in which X is F, Cl, —CF$_3$, —CHF$_2$, —OCF$_3$ or —OCHF$_2$.

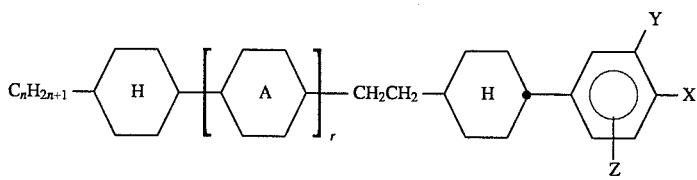

in which n is 1 to 7, r is 0 or 1, the ring A is trans-1,4-cyclohexylene or 1,4-phenylene, X is F, Cl, —CF$_3$, —CN, —OCF$_3$ or —OCHF$_2$, and Y and Z are each, independently of one another, H or F, with the proviso that, in the case where r=1, A=1,4-phenylene and X=F or Cl, Y and/or Z are fluorine.

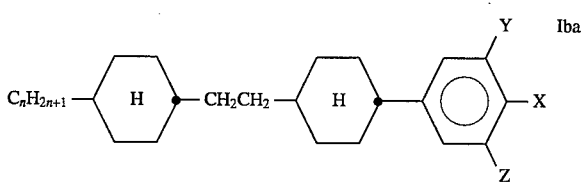

in which X is —CHF$_2$, —CF$_3$, —OCF$_3$ or —OCHF$_2$, and Y and Z are each, independently of one another, H or F.

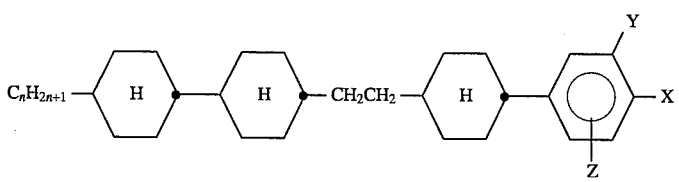

in which X, Y and Z are as defined in claim 8, preferably
(a) X=CN, Y=F and Z=H,
(b) X=F, C 1, —CF₃ , —OCF₃ or —OCHF₂, and Y=Z=H,
(c) X=F, Cl, —CF₃, —OCF₃ or —OCHF₂, in particular F or Cl, Y=F and Z=H. X=F, Cl, —CF₃, —OCF₃ or —OCHF₂, Y=F and Z=H
(X=F or Cl is particularly preferred).

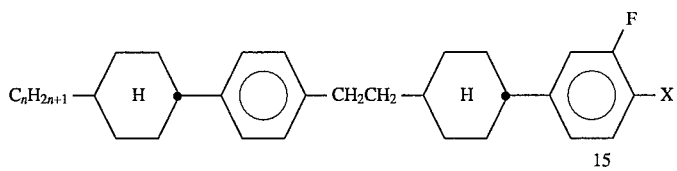

Ibe in which X is preferably F or Cl.

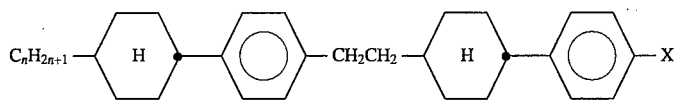

Ibf in which X is preferably —CN, —CHF₂, —CF₃, —OCF₃ or —OCHF₂, particularly preferably —CF₃, —OCF₃ or —OCHF₂.

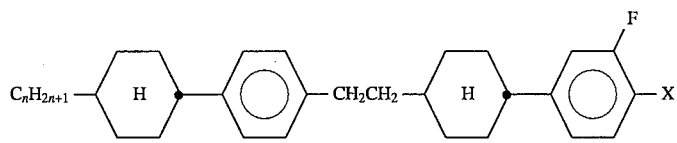

Ibg in which X is preferably —CN, —CF₃, —OCF₃ or —OCHF₂.

Particular preference is furthermore given to the compounds of the following sub-formulae:

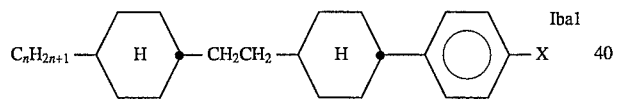

Iba1 in which X is preferably —CF₃ , —OCF₃ or —OCHF₂ ,

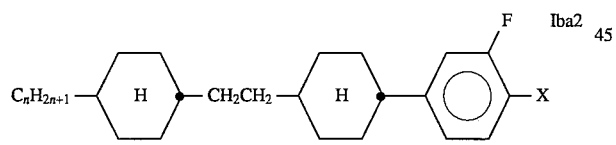

Iba2 in which X is preferably —CF₃, —OCF₃ or —OCHF₂,

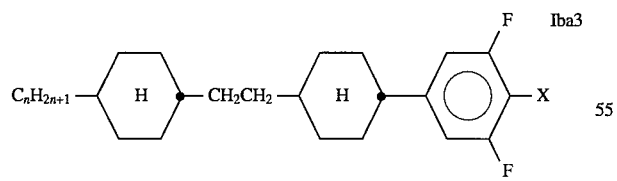

Iba3 in which X is preferably F, Cl, —CF₃,—CN, —OCF₃ or —OCHF₂.

In addition, the compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. Use may also be made here of variants which are known per se, but are not described here in greater detail.

If desired, the starting materials can also be formed in situ by not isolating them from the reaction mixture, but instead immediately reacting them further to form the compounds of the formula I.

The compounds of the formula I in which r=1 and A is trans-1,4-cyclohexylene can be obtained, for example, by reacting an aldehyde of the formula II

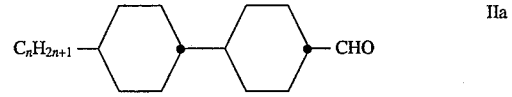

IIa with a phosphonium salt, for example an appropriate p(substituted phenyl)-benzyl bromide, by the Wittig method, and catalytic hydrogenation, for example on Pd/C, of the ethene derivatives obtained.

Precursors which are suitable for synthesis of the benzyl bromides can be obtained, for example, by the following synthesis scheme:

Scheme 1

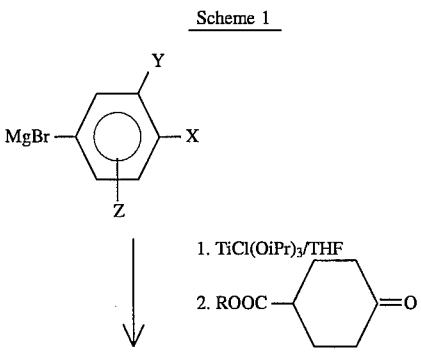

-continued
Scheme 1

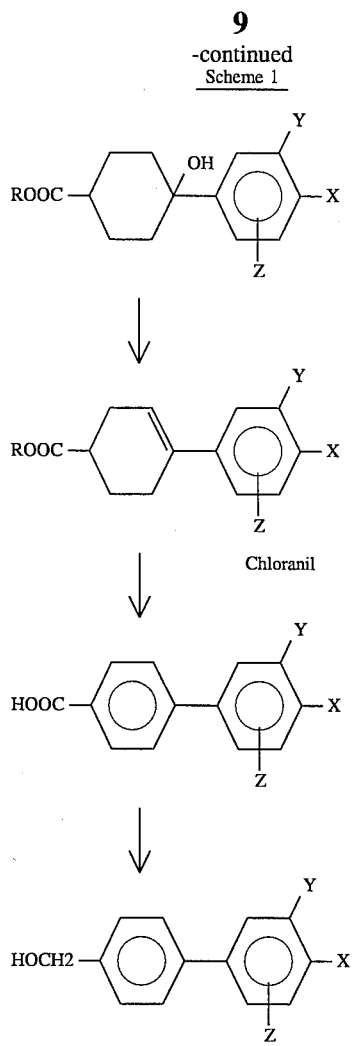

The Grignard compound obtained from the corresponding bromobenzene derivative is reacted with chlorotrialkyl orthotitanate or -zirconate by the method of WO 87/05599 to give the tertiary cyclohexanol. The elimination of water, dehydration and reduction to the benzyl alcohol give the suitable precursors.

Some of the bromobenzene derivatives used as starting materials are known, and some can be prepared without difficulty by standard methods of organic chemistry from compounds caused by [sic] the literature. For example, the OCF$_3$- or OCHF$_2$-compounds can be obtained by known processes from the corresponding phenols, the CHF$_2$-compounds can be obtained from the corresponding aldehydes, and the CF$_3$- or CN-compounds can be obtained from the corresponding benzoic acids. Compounds of the formula

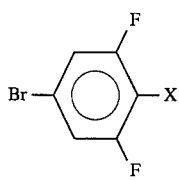

or corresponding monofluorinated compounds can be obtained, for example, from the known precursors where X=H by lithiation at low temperatures and subsequent reaction with a suitable electrophile.

The compounds of the formula I where B=3-fluoro-1,4-phenylene are obtained entirely analogously by using

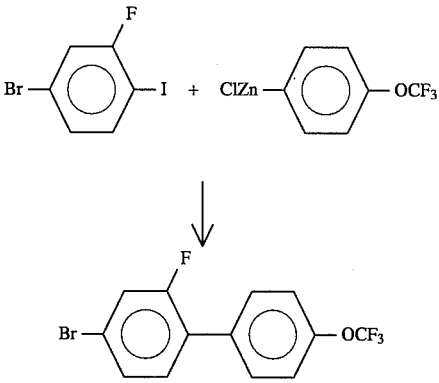

in place of the bromobenzene derivatives. The bromobiphenyls can be prepared in a manner known per se by cross-coupling reactions catalyzed by noble metals (E. Poetsch, Kontakte (Darmstadt) 1988 (2) p. 15).

An illustrative variant is given below:

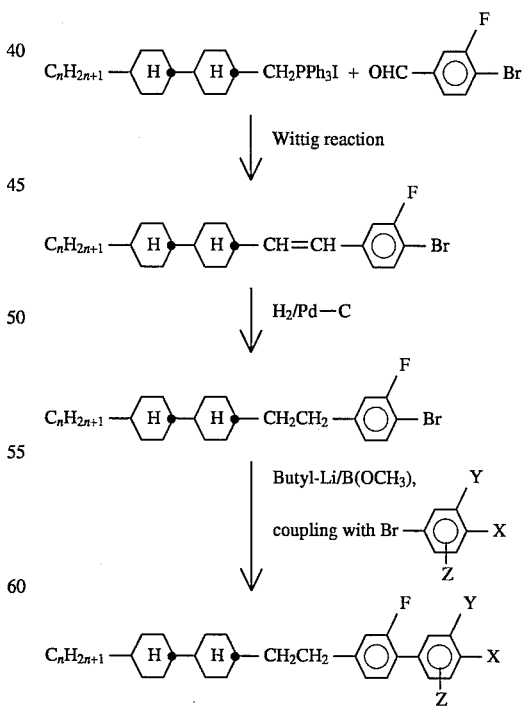

Other synthesis variants are known to those skilled in the art. Preferred variants are given in the following schemes. All the starting materials are either known or can be prepared analogously to known compounds.

Scheme 2

Scheme 3
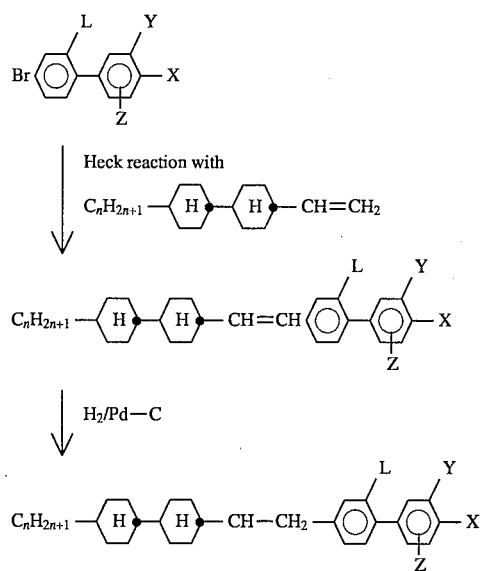
Scheme 4
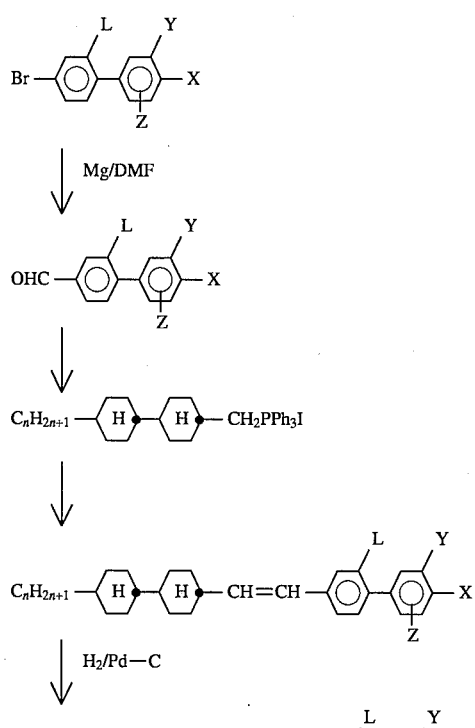
Scheme 5
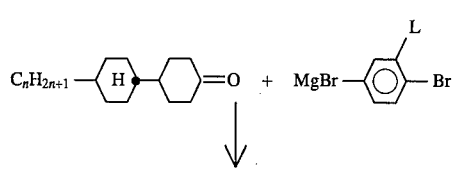
Scheme 5 (continued)
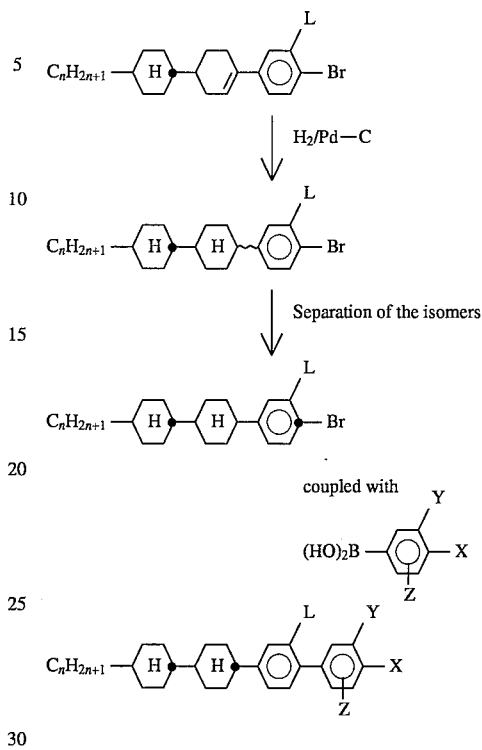
Scheme 6a
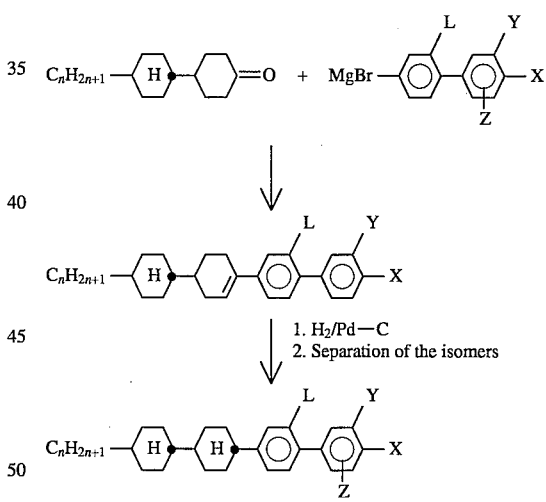
Schema 6b
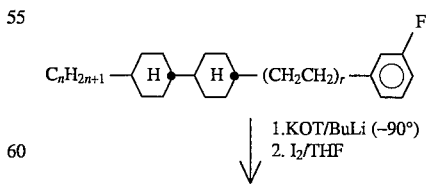

13
-continued
Schema 6b

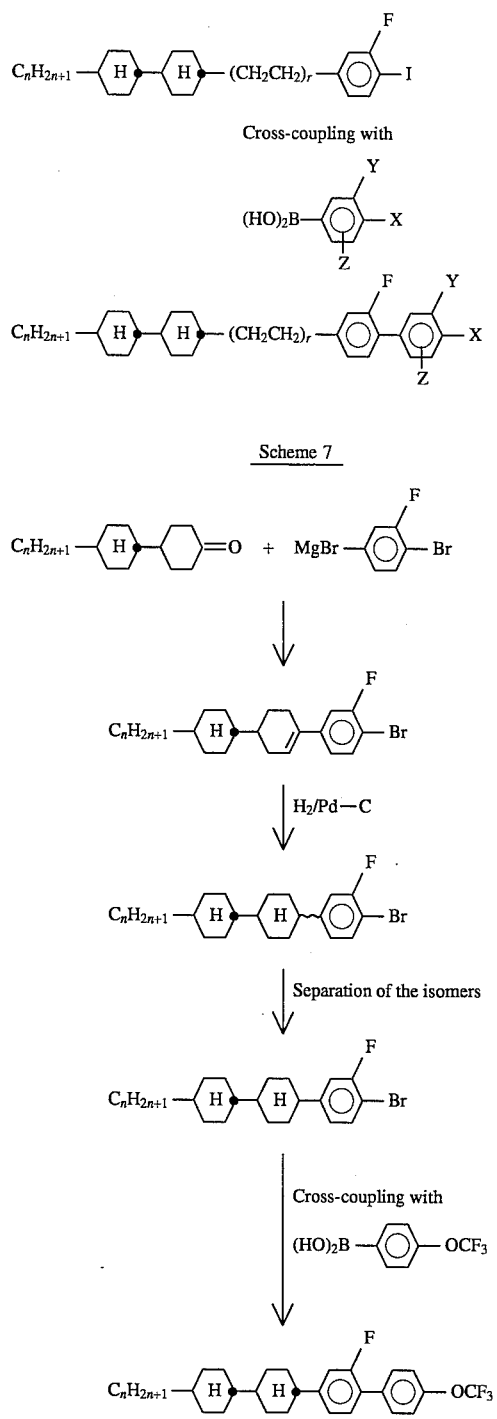

Scheme 7

Scheme 8

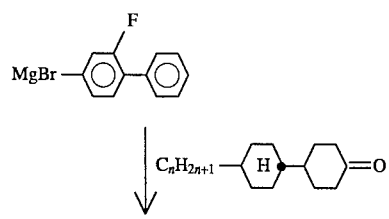

14
-continued
Scheme 8

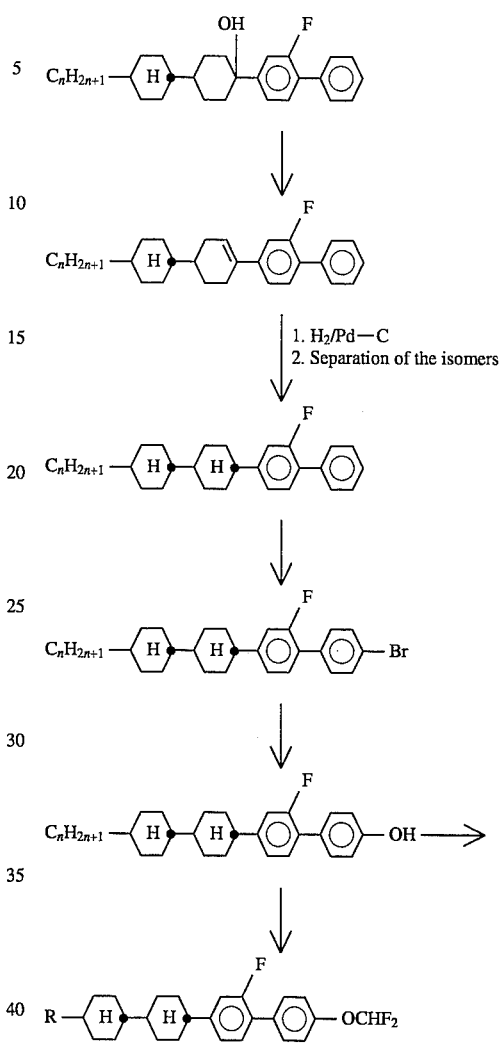

The compounds of the formula Ib can be obtained, for example, by reacting an aldehyde of the formula IIb

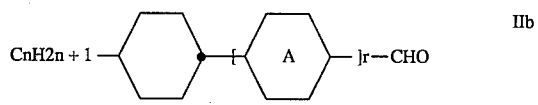

with the phosphonium salt of an appropriate trans-4(subst. phenyl)-cyclohexylmethyl bromide by the Wittig method, and catalytic hydrogenation, for example on Pd/C, of the ethene derivatives obtained.

Suitable precursors for the synthesis of the cyclohexylmethyl bromides can be obtained, for example, by the following synthesis scheme:

Scheme 9

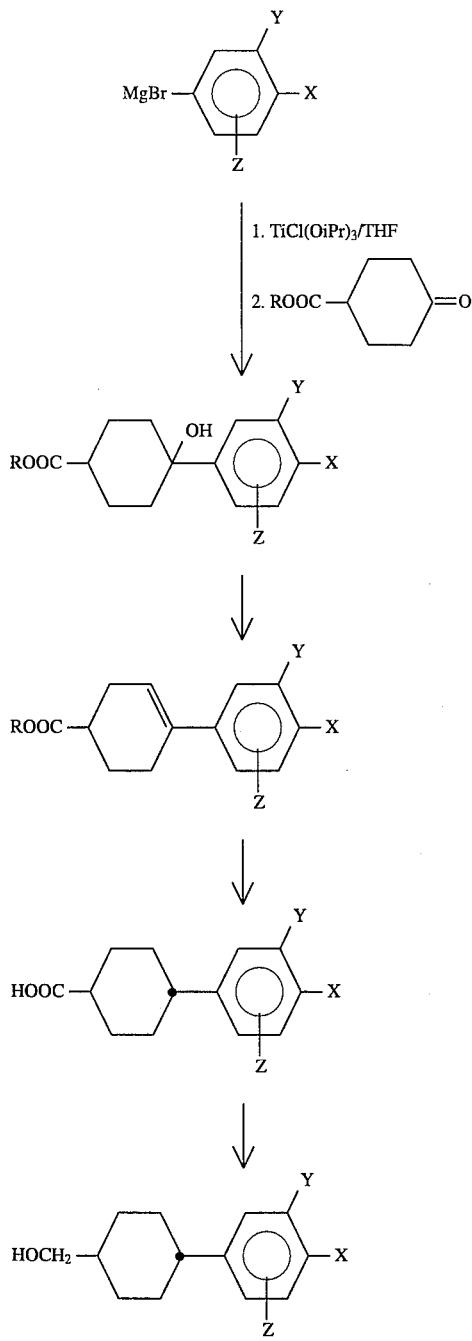

The Grignard compound obtained from the corresponding bromobenzene derivative is reacted with chlorotrialkyl orthotitanate or -zirconate by the method of WO 87/05599 to give the tertiary cyclohexanol. Elimination of water, hydrogenation, isomerization and reduction to the cyclohexylmethyl alcohol give the suitable precursors.

Further synthesis variants are known to those skilled in the art. Preferred variants are given in the following schemes. All the starting materials are either known or can be prepared analogously to known compounds. The cyclohexylacetyl chloride in Scheme 11 can be prepared by customary homologization of the corresponding cyclohexanecarboxylic acid from Scheme 9.

Scheme 10

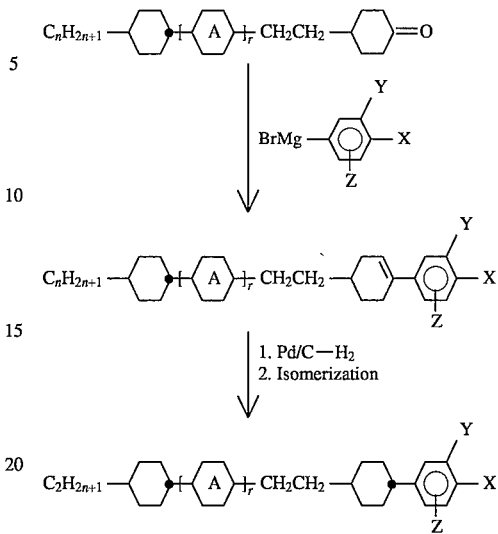

Scheme 11

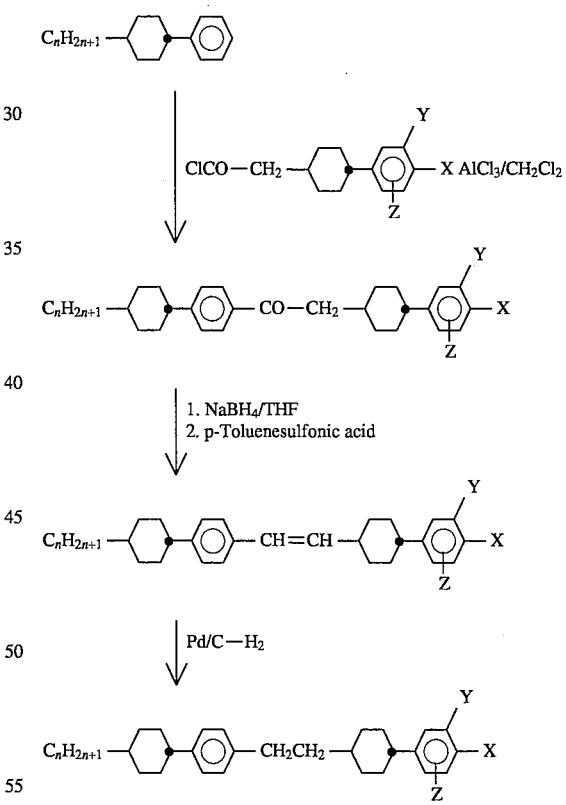

Further possible syntheses of preferred nitriles of the formula I are given in Schemes 12 and 13 below:

Scheme 12

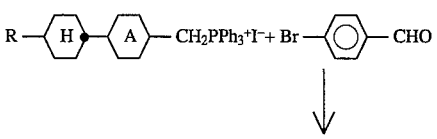

Scheme 12 -continued
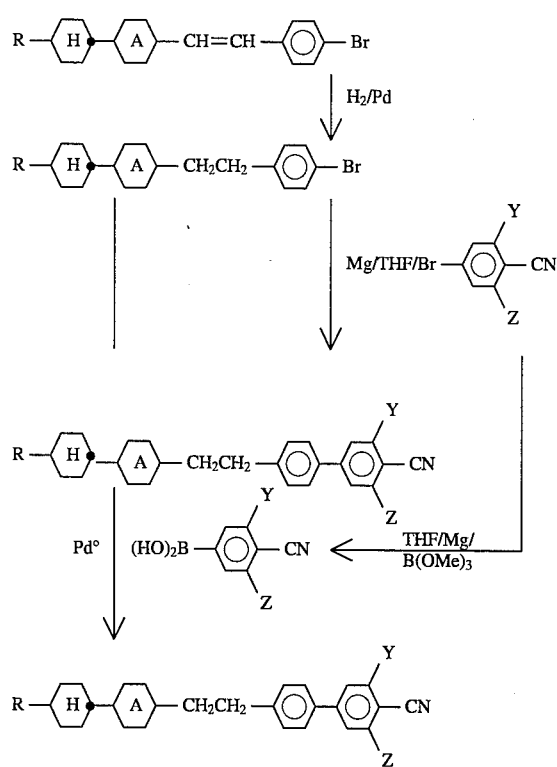
Scheme 13
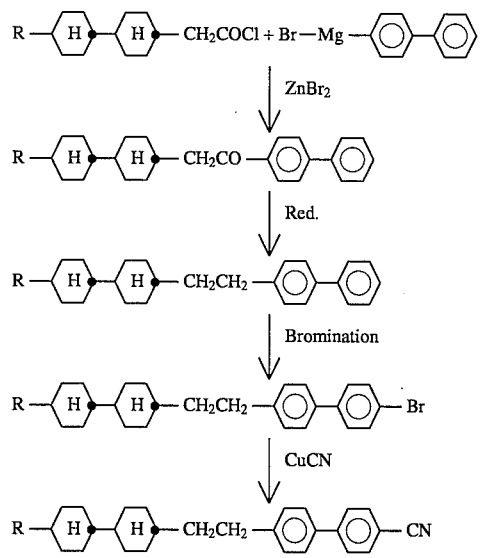
Further synthesis schemes for particularly preferred compounds.
Scheme 14
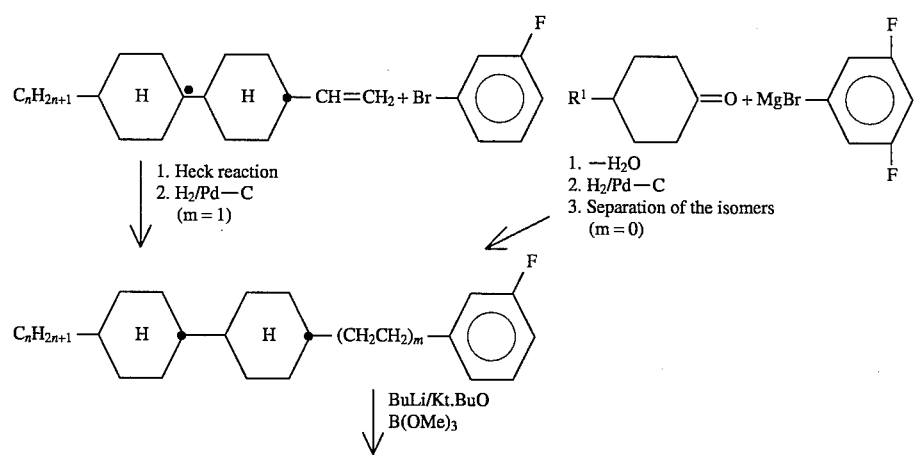

-continued
Scheme 14

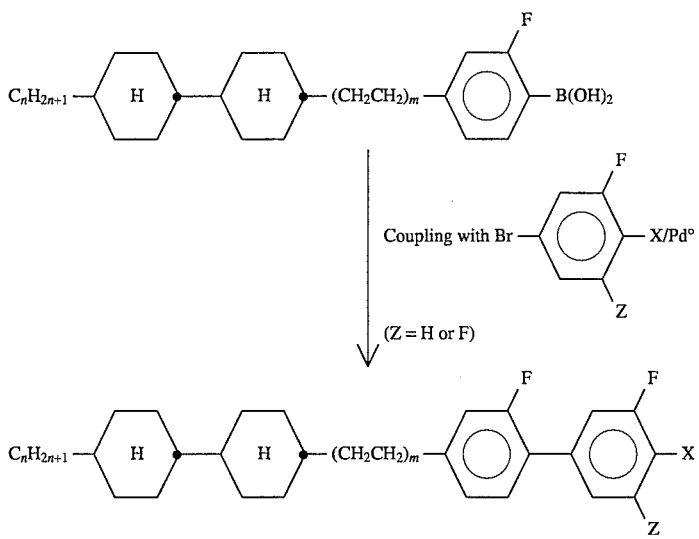

(Z = H or F)

Scheme 15

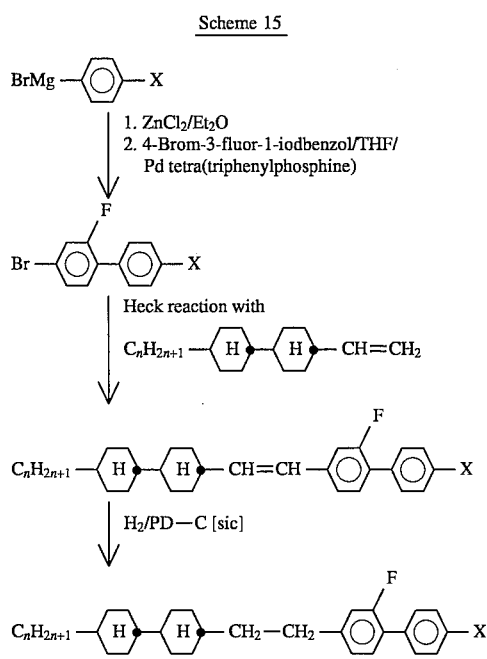

Scheme 16

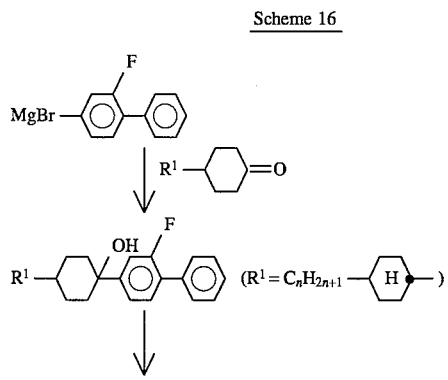

-continued
Scheme 16

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

$$R'-L-E-R'' \quad 1$$

$$R'-L-COO-E-R'' \quad 2$$

$$R'-L-OOC-E-R'' \quad 3$$

$$R'-L-CH_2CH_2-E-R'' \quad 4$$

$$R'-L-C\equiv C-E-R'' \quad 5$$

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radical L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In a smaller sub-group of the compounds of the formulae 1, 2, 3, 4 and 5, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labeled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5 which is known as group B, R" is —F, —Cl, —NCS or —(O)$_i$CH$_{3-(k+1)}$F$_k$Cl$_L$, where i is 0 or 1, and k+1 is 1, 2 or 3; the compounds in which R" has this meaning are labeled with the sub-formulae 1b, 2b, 3b, 4b and 5b. Particular preference is given to those compounds of the sub-formulae 1b, 2b, 3b, 4b and 5b in which R" is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is —CN; this subgroup is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably contain one or more compounds selected from group A and/or group B and/or group C. The proportions by weight of the compounds from these groups in the media according to the invention are preferably Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular media according to the invention preferably being 5% –90% and in particular 10% to 90%.

The media according to the invention preferably contain 1 to 40%, particularly preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed.

Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The examples below are intended to illustrate the invention without representing a limitation. mp.=melting point, cp.=clear point. Above and below, percent data are percent by weight. All temperatures are given in degrees Celsius. "Customary work-up" means that water is added, the mixture is extracted with methylene chloride, the organic phase is separated off, dried and evaporated, and the product is purified by crystallization and/or chromatography.

Furthermore: C: crystalline solid state, S: smectic phase (the index characterizes the phase type), N: nematic state, Ch: cholesteric phase, I: isotropic phase. The number between two symbols indicates the conversion temperature in degrees Celsius.

In the present application and in the examples below, the structures of the liquid-crystal compounds are indicated by acronyms, the transformation into chemical formulae taking place as in Tables A and B below. All the radicals $C_nH_{2n+1}$ and $C_mH_{2m+1}$ are straight-chain alkyl radicals containing n or m carbon atoms. The coding in Table B requires no further explanation. In Table A, only the 10 acronym for the parent structure is given. In individual cases, a code follows for the substituents $R^1$, $R^2$, $L^1$ and $L^2$, separated from the acronym for the parent structure by a hyphen:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| nT | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nOmFF | $C_nH_{2n+1}$ | $OC_mH_{2m+1}$ | F | F |
| nmF | $C_nH_{2n+1}$ | $C_mH_{2m+1}$ | F | H |
| nCF$_3$ | $C_nH_{2n+1}$ | $CF_3$ | H | H |
| nOCF$_3$ | $C_nH_{2n+1}$ | $OCF_3$ | H | H |
| nOCF$_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_3H_{2s}$— | CN | H | H |
| rEsN | $C_rH_{2r+1}$—O—$C_3H_{2s}$— | CN | H | H |
| nNF | $C_nH_{2n+1}$ | CN | F | H |
| nAm | $C_nH_{2n+1}$ | $COOC_mH_{2m+1}$ | H | H |

TABLE A

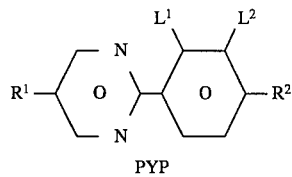

PYP

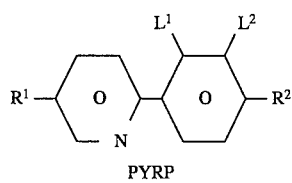

PYRP

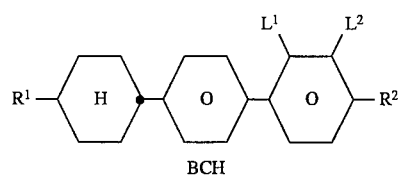

BCH

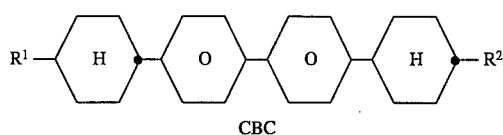

CBC

TABLE A-continued

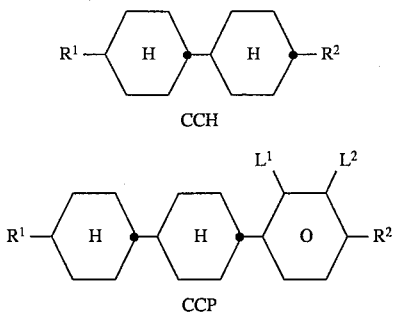

CCH

CCP

TABLE A-continued

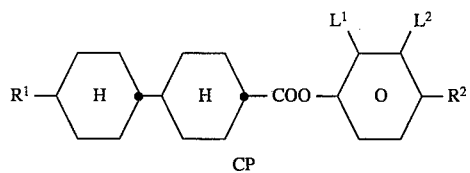

CP

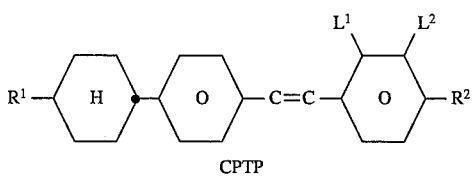

CPTP

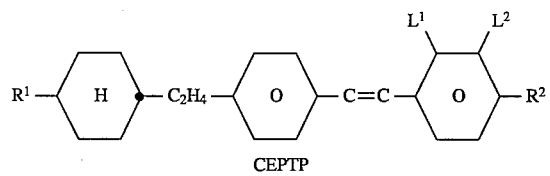

CEPTP

TABLE A-continued
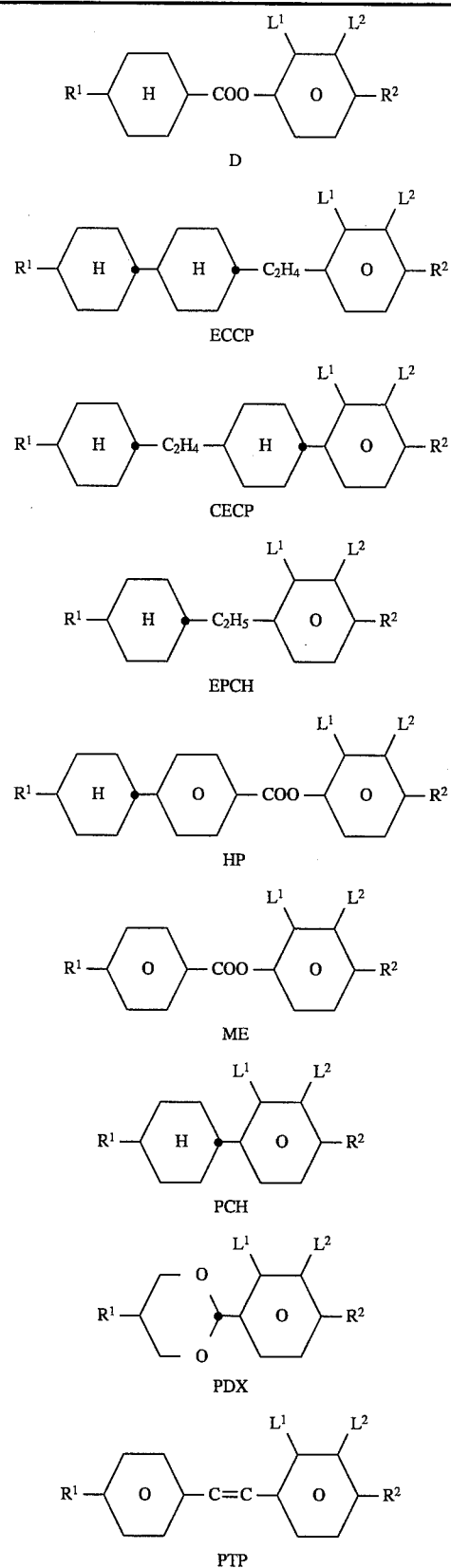
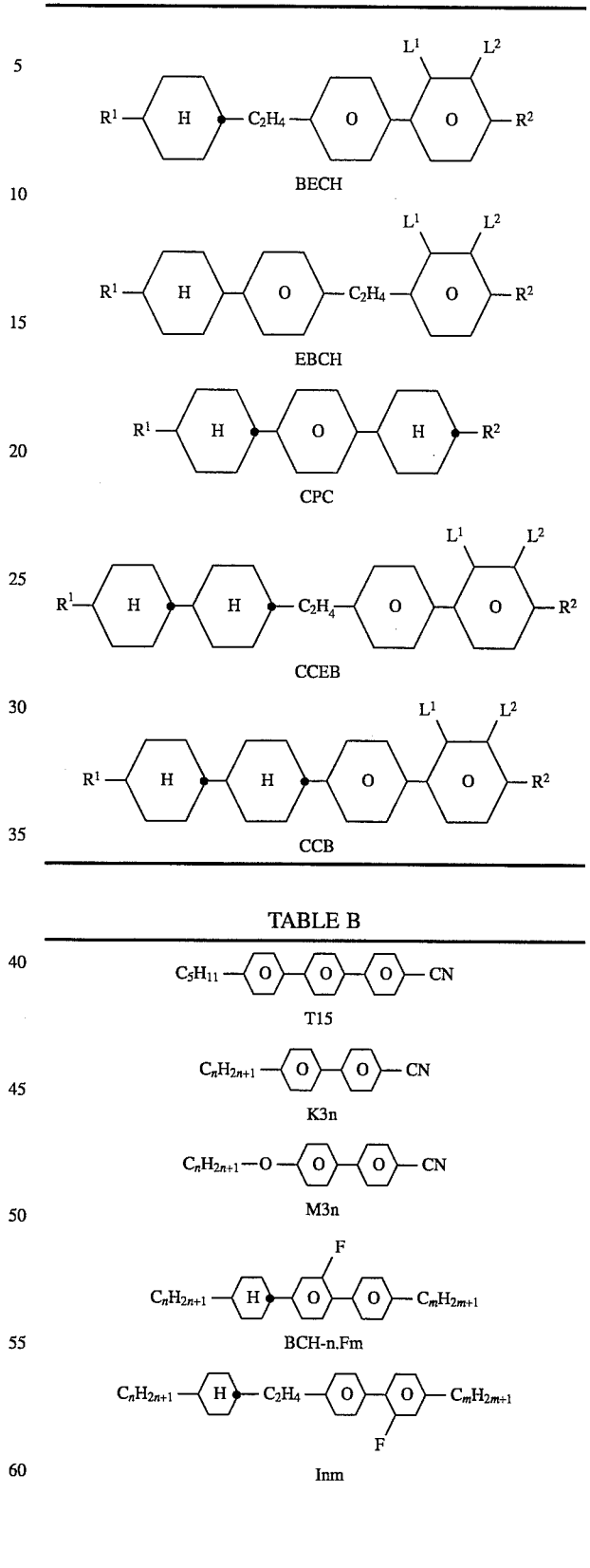
TABLE B

TABLE B-continued

C-nm: $C_nH_{2n+1}$—[H]—[H]—OOC—$C_mH_{2m+1}$

C15: $C_2H_5$—CH(CH$_3$)*—CH$_2$—O—[O]—[O]—CN

CB15: $C_2H_5$—CH(CH$_3$)*—CH$_2$—[O]—[O]—CN

CBC-nmF: $C_nH_{2n+1}$—[H]—[O]—[O]—[H]—$C_mH_{2m+1}$ (F on ring)

CCB-n.FX: $C_nH_{2n+1}$—[H]—[H]—[O]—[O]—X (F)

CCEB-n.FX: $C_nH_{2n+1}$—[H]—[H]—C$_2$H$_4$—[O]—[O]—X (F)

CCN-nm: $C_nH_{2n+1}$—[H]—[H](CN)—$C_mH_{2m+1}$

CCPC-nm: $C_nH_{2n+1}$—[H]—[H]—COO—[O]—[H]—$C_mH_{2m+1}$

CH-nm: $C_nH_{2n}$—[H]—[H]—COO—[H]—$C_mH_{2m+1}$

HD-nm: $C_nH_{2n+1}$—[H]—[O]—OOC—[H]—$C_mH_{2m+1}$

HH-nm: $C_nH_{2n+1}$—[H]—[O]—COO—[H]—$C_mH_{2m+1}$

NCB-nm: $C_nH_{2n+1}$—[O]—[O]—[H](CN)—$C_mH_{2m+1}$

OS-nm: $C_nH_{2n+1}$—[H]—COO—[H]—$C_mH_{2m+1}$

CHE: $C_2H_5$—[H]—COO—[O]—[O]—CN

ECBC-nm: $C_nH_{2n+1}$—[H]—C$_2$H$_4$—[O]—[O]—[H]—$C_mH_{2m+1}$

ECCH-nm: $C_nH_{2n+1}$—[H]—C$_2$H$_4$—[H]—$C_mH_{2m+1}$

CCH-n1Em: $C_nH_{2n+1}$—[H]—[H]—CH$_2$O—$C_mH_{2m+1}$

T-nFn: $C_nH_{2n+1}$—[O]—[O]—[O]—CN (F)

| | |
|---|---|
| DAST | diethylaminosulfur trifluoride |
| DCC | dicyclohexylcarbodiimide |
| DDQ | dichlorodicyanobenzoquinone |
| DIBALH | diisobutylaluminum hydride |
| DMSO | dimethyl sulfoxide |
| POT | potassium tertiary-butanolate |
| THF | tetrahydrofuran |
| pTSOH | p-toluenesulfonic acid |

EXAMPLE 1

A solution of 0.05 m of 1-[trans-4-(trans-4-n-propylcyclohexyl)cyclohexyl]-2-(p-bromophenyl)ethane (DE 3317597) and 0.05 m of p-trifluoromethylphenylboric acid (prepared from p-bromotriflurotoluene by consecutive reaction with n-BuLi/B(OCH$_3$)$_3$ and H$^+$/H$_2$O) in 100 ml of toluene and 50 ml of ethanol is refluxed for 4 hours after 0.0001 m of Pd(Ph$_3$)$_4$ and 50 ml of Na$_2$CO$_3$ solution (2M) have been added, Conventional extractive work-up and subsequent purification by chromatography and crystallization give 1-[trans-4-(trans-4-n-propylcyclohexyl)-cyclohexyl]-2-(4-trifluoromethylbiphenyl-4'-yl)ethane,

EXAMPLES 2 to 62

The following compounds of the sub-formula Ia are obtained analogously to Example 1:

| | n | X | Y | Z | s | L |
|---|---|---|---|---|---|---|
| (2) | 2 | —CF$_3$ | H | H | 1 | H |
| (3) | 5 | —CF$_3$ | H | H | 1 | H |
| (4) | 4 | —CF$_3$ | H | H | 1 | H |
| (5) | 5 | F | H | H | 1 | H |
| (6) | 2 | F | H | H | 1 | H |
| (7) | 3 | F | H | H | 1 | H |
| (8) | 5 | Cl | H | H | 1 | H |
| (9) | 2 | Cl | H | H | 1 | H |
| (10) | 3 | Cl | H | H | 1 | H, C 13.5 N 284 I |
| (11) | 5 | Cl | F | H | 1 | H |
| (12) | 5 | Cl | F | H | 1 | H |
| (13) | 3 | Cl | F | H | 1 | H, C 82 N 263 I |
| (14) | 5 | F | F | H | 1 | F |
| (15) | 2 | F | F | H | 1 | F |
| (16) | 3 | F | F | H | 1 | F |
| (17) | 2 | —OCF$_3$ | H | H | 1 | H |
| (18) | 3 | —OCF$_3$ | H | H | 1 | H |
| (19) | 5 | —OCF$_3$ | H | H | 1 | H |
| (20) | 2 | —OCF$_3$ | H | H | 1 | F |
| (21) | 3 | —OCF$_3$ | H | H | 1 | F |
| (22) | 5 | —OCF$_3$ | H | H | 1 | F |
| (23) | 2 | —CF$_3$ | H | H | 1 | F |
| (24) | 3 | —CF$_3$ | H | H | 1 | F |
| (25) | 5 | —CF$_3$ | H | H | 1 | F |
| (26) | 2 | F | F | H | 0 | F |
| (27) | 3 | F | F | H | 0 | F |

-continued

| | n | X | Y | Z | s | L |
|---|---|---|---|---|---|---|
| (28) | 5 | F | F | H | 0 | F |
| (29) | 2 | F | H | H | 0 | F |
| (30) | 3 | F | H | H | 0 | F |
| (31) | 5 | F | H | H | 0 | F |
| (32) | 2 | Cl | H | H | 0 | F |
| (33) | 3 | Cl | H | H | 0 | F |
| (34) | 5 | Cl | H | H | 0 | F |
| (35) | 2 | OCF$_3$ | H | H | 0 | F |
| (36) | 3 | OCF$_3$ | H | H | 0 | F |
| (37) | 4 | OCF$_3$ | H | H | 0 | F |
| (38) | 5 | OCF$_3$ | H | H | 0 | F |
| (39) | 2 | OCHF$_2$ | H | H | 0 | F |
| (40) | 3 | OCHF$_2$ | H | H | 0 | F |
| (41) | 4 | OCHF$_2$ | H | H | 0 | F |
| (42) | 5 | OCHF$_2$ | H | H | 0 | F |
| (43) | 2 | Cl | F | H | 0 | H |
| (44) | 3 | Cl | F | H | 0 | H |
| (45) | 4 | Cl | F | H | 0 | H |
| (46) | 5 | Cl | F | F | 0 | H |
| (47) | 2 | Cl | F | F | 0 | H |
| (48) | 3 | Cl | F | F | 0 | H |
| (49) | 4 | Cl | F | F | 0 | H |
| (50) | 5 | Cl | F | F | 0 | H |
| (51) | 2 | F | F | F | 0 | H |
| (52) | 3 | F | F | F | 0 | H |
| (53) | 4 | F | F | F | 0 | H |
| (54) | 5 | F | F | F | 0 | H |
| (55) | 2 | CF$_3$ | F | F | 0 | H |
| (56) | 3 | CF$_3$ | F | F | 0 | H |
| (57) | 4 | CF$_3$ | F | F | 0 | H |
| (58) | 5 | CF$_3$ | F | F | 0 | H |
| (59) | 2 | OCHF$_2$ | F | H | 0 | H |
| (60) | 3 | OCHF$_2$ | F | H | 0 | H |
| (61) | 4 | OCHF$_2$ | F | H | 0 | H |
| (62) | 5 | OCHF$_2$ | F | H | 0 | H |

EXAMPLE 63 a) 0.2 m of n-BuLi and subsequently a solution of 0.2 m TiCl (OiPr)$_3$ in THF are added to a solution of 0.2 m of 3,4-difluorobromobenzene in 100 ml of diethyl ether at −30°. The temperature is then allowed to reach −10° with stirring, 0.2 m of ethyl 4-oxocyclohexanecarboxylate is added, and the mixture is stirred at room temperature for a further 2 hours. After extractive work-up and removal of the solvent, the residue is taken up in 200 ml of toluene, 1 g of p-toluenesulfonic acid is added, and tile mixture is boiled for 2 hours on a water separator. After extractive work-up, the product is purified by chromatography.

b) The cyclohexene derivative obtained is dissolved in 100 ml of THF, 5 g of Pd/C are added, and the mixture is hydrogenated at atmospheric pressure. Filtration, evaporation, ether cleavage under basic conditions and crystallization give trans-4-(3,4-difluorophenyl)cyclohexanecarboxylic acid.

c) The cyclohexanecarboxylic acid obtained is stirred overnight at room temperature with 50 ml of thionyl chloride. After distillative purification, the acid chloride is converted into the aldehyde by the Rosenmund method by passing in hydrogen in the presence of Pd/BaSO$_4$.

d) POT is added with cooling at 0° to a stirred solution of 0.1 m of the resultant aldehyde and 0.1 m of trans-4-(trans-4-n-propylcyclohexyl)cyclohexyl-methylphosphonium iodide in 100 ml of THF. The mixture is stirred at room temperature for a further 4 hours and, after 50 ml of H$_2$O have been added, worked up by extraction.

e) The crude product is hydrogenated at atmospheric pressure after 5 g of Pd/C in THF have been added. Filtration, evaporation and purification by crystallization give 1-[trans-4-(trans-4-n-propylcyclohexyl)cyclohexyl]-2-[trans-4-(3,4-difluorophenyl)cyclohexyl]ethane.

EXAMPLES 64 to 126

The following compounds of the sub-formula Ib are obtained analogously to Example 63:

| | n | X | Y | Z | r | A |
|---|---|---|---|---|---|---|
| (64) | 2 | —CF$_3$ | H | H | 0 | — |
| (65) | 5 | —CF$_3$ | H | H | 0 | — |
| (66) | 4 | —CF$_3$ | H | H | 0 | — |
| (67) | 5 | F | F | F | 0 | — |
| (68) | 2 | F | F | F | 0 | — |
| (69) | 3 | F | F | F | 0 | — |
| (70) | 5 | Cl | F | F | 0 | — |
| (71) | 2 | Cl | F | F | 0 | — |
| (72) | 3 | Cl | F | F | 0 | — |
| (73) | 5 | —OCF$_3$ | H | H | 0 | — |
| (74) | 2 | —OCF$_3$ | H | H | 0 | — |
| (75) | 3 | —OCF$_3$ | H | H | 0 | — |
| (76) | 5 | —OCHF$_2$ | H | H | 0 | — |
| (77) | 2 | —OCHF$_2$ | H | H | 0 | — |
| (78) | 3 | —OCHF$_2$ | H | H | 0 | — |
| (79) | 2 | F | H | H | 1 | Cy |
| (80) | 3 | F | H | H | 1 | Cy |
| (81) | 5 | F | H | H | 1 | Cy |
| (82) | 2 | Cl | H | H | 1 | Cy |
| (83) | 3 | Cl | H | H | 1 | Cy |
| (84) | 5 | Cl | H | H | 1 | Cy |
| (85) | 2 | F | F | H | 1 | Cy |
| (86) | 4 | F | F | H | 1 | Cy |
| (87) | 5 | F | F | H | 1 | Cy |
| (88) | 2 | Cl | F | H | 1 | Cy |
| (89) | 3 | Cl | F | H | 1 | Cy |
| (90) | 5 | Cl | F | H | 1 | Cy |
| (91) | 2 | —CF$_3$ | H | H | 1 | Cy |
| (92) | 3 | —CF$_3$ | H | H | 1 | Cy |
| (93) | 5 | —CF$_3$ | H | H | 1 | Cy |
| (94) | 3 | —CF$_3$ | F | H | 1 | Cy |
| (95) | 3 | —CF$_3$ | F | H | 1 | Cy |
| (96) | 5 | —CF$_3$ | F | H | 1 | Cy |
| (97) | 2 | —CN | H | H | 1 | Cy |
| (98) | 3 | —CN | H | H | 1 | Cy |
| (99) | 5 | —CN | H | H | 1 | Cy |
| (100) | 2 | —CN | F | H | 1 | Cy |
| (101) | 3 | —CN | F | H | 1 | Cy |
| (102) | 5 | —CN | F | H | 1 | Cy |
| (103) | 2 | —CN | F | F* | 1 | Cy |
| (104) | 3 | —CN | F | F* | 1 | Cy |
| (105) | 5 | —CN | F | F* | 1 | Cy |
| (106) | 2 | —OCF$_3$ | H | H | 1 | Cy |
| (107) | 3 | —OCF$_3$ | H | H | 1 | Cy |
| (108) | 5 | —OCF$_3$ | H | H | 1 | Cy |
| (109) | 2 | —OCHF$_2$ | H | H | 1 | Cy |
| (110) | 3 | —OCHF$_2$ | H | H | 1 | Cy |
| (111) | 5 | —OCHF$_2$ | H | H | 1 | Cy |
| (112) | 2 | F | F | H | 1 | Ph |
| (113) | 3 | F | F | H | 1 | Ph |
| (114) | 5 | F | F | H | 1 | Ph |
| (115) | 2 | Cl | F | H | 1 | Ph |
| (116) | 3 | Cl | F | H | 1 | Ph |
| (117) | 5 | Cl | F | H | 1 | Ph |
| (118) | 2 | —CN | H | H | 1 | Ph |
| (119) | 3 | —CN | H | H | 1 | Ph |
| (120) | 5 | —CN | H | H | 1 | Ph |
| (121) | 2 | —CF$_3$ | H | H | 1 | Ph |
| (122) | 3 | —CF$_3$ | H | H | 1 | Ph |
| (123) | 5 | —CF$_3$ | H | H | 1 | Ph |
| (124) | 2 | —OCF$_3$ | H | H | 1 | Ph |
| (125) | 3 | —OCF$_3$ | H | H | 1 | Ph |
| (126) | 5 | —OCF$_3$ | H | H | 1 | Ph |

*Z in the ortho-position to X

EXAMPLE 127

In accordance with Scheme 12 above, 3 g of 1-(trans, trans-4-n-propylcyclohexylcyclohexyl)-2-(p-bromophenyl)ethane are refluxed with 1.13 g of p-cyanophenylboric acid and 0.01 g of tetrakistriphenylphosphine Pd (0) in 20 ml of toluene with 2M sodium carbonate solution (10 ml) and 4 ml of ethanol until the reaction is complete. Customary work-up gives 1-(trans,trans-4-n-propylcyclohexylcyclohexyl)-2-(4-cyanobiphenyl-4'-yl)ethane, C 139N>300 I.

The following compounds of the sub-formula Iaa are obtained analogously

| n | s | X |
|---|---|---|
| 1 | 1 | CN |
| 2 | 1 | CN |
| 4 | 1 | CN |
| 5 | 1 | CN |
| 6 | 1 | CN |
| 7 | 1 | CN |
| 8 | 1 | CN |
| 9 | 1 | CN |
| 10 | 1 | CN |
| 2 | 1 | $OCF_3$ |
| 3 | 1 | $OCF_3$ |
| 5 | 1 | $OCF_3$ |
| 2 | 1 | $OCHF_2$ |
| 3 | 1 | $OCHF_2$ |
| 5 | 1 | $OCHF_2$ |

EXAMPLE 128

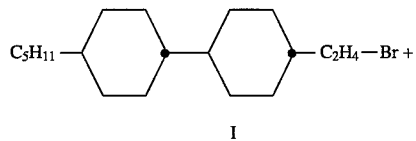

I

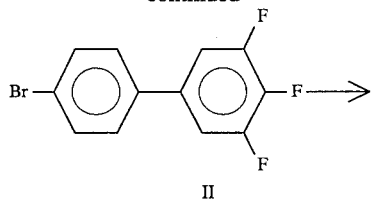

II

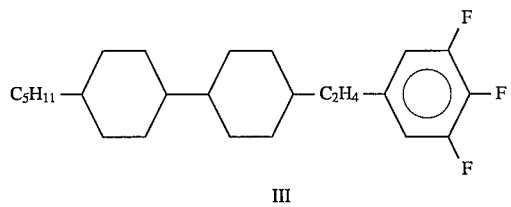

III 11.5 g of anhydrous zinc bromide and then 1.4 g of lithium granules are added to 0.1 mol of I in 150ml of a THF/toluene solvent mixture (1:4 ratio by volume). The mixture is treated with ultrasound for 4 hours at between 0° C. and 10° C. under argon and with stirring in order to convert I into the corresponding dialkyl zinc compound. 0.1 mol of II and 1.5 g (2 mol %) of 1,1'-bis(diphenylphosphino)ferrocene/palladium(II) dichloride ($PdCl_2$ dppf) are added to the organozinc compound, and the mixture is stirred at room temperature for 24 hours after removal of the ultrasound bath and of the cooling. The mixture is decomposed using 100 ml of saturated $NH_4Cl$ solution with stirring, the organic phase is separated off, and the aqueous phase is extracted twice with toluene. Drying, evaporation and chromatographing of the combined organic extracts on silica gel using hexane give III.

EXAMPLE 129

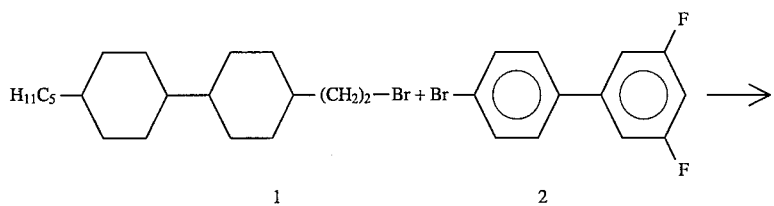

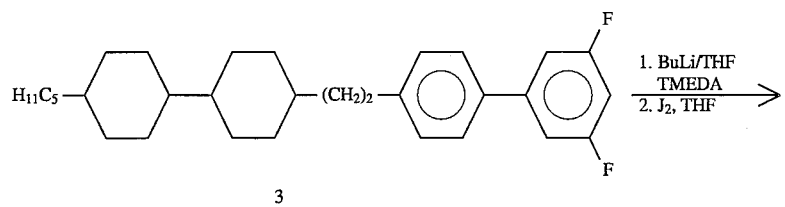

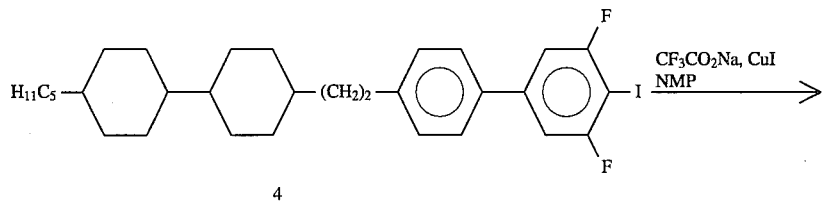

-continued

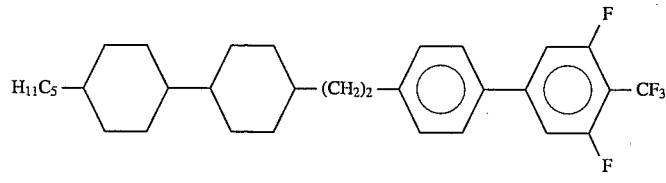

5

100 mmol of 1 are converted into 3 by reaction with 2 analogously to the above example.

31 ml of n-BuLi (15% in hexane) are added drop-wise to a mixture of 47 mmol of 3, 7.5 ml of TMEDA (50 mmol) and 150 ml of THF at –65° to –70 ° C., and the mixture is stirred for a further 1 hour at –70 ° C. A solution 12.0 g (47 mmol) of iodine in 25 ml of THF is then added dropwise at –65° to –70° C., and the mixture is stirred at –70° C. for 0.5 hours. The mixture is warmed to –30° C., hydrolyzed using 15 ml of water, and the excess iodine is reduced by adding 15 ml of sodium bisulfite solution. Customary work-up and recrystallization from hexane give 4. 400 ml of NMP are removed from a mixture of 38 mmol of 4, 4.4 g (76 mmol) of KF, 22.8 g (168 mmol) of sodium trifluoroacetate and 800 ml of NMP by distillation at 70° C. and 4 mbar. 1.4 g (76 mmol) of dried CuI are then added to the reaction mixture, which is stirred at 160° C. for 5 hours. About 300 ml of NMP are then removed by distillation. The mixture is allowed to cool to RT, and 400 ml of MTB ether are added. The mixture is washed with water, dried with $Na_2SO_4$, filtered and evaporated to give a residue. Chromatography on silica gel using hexane gives 5.

EXAMPLE 130

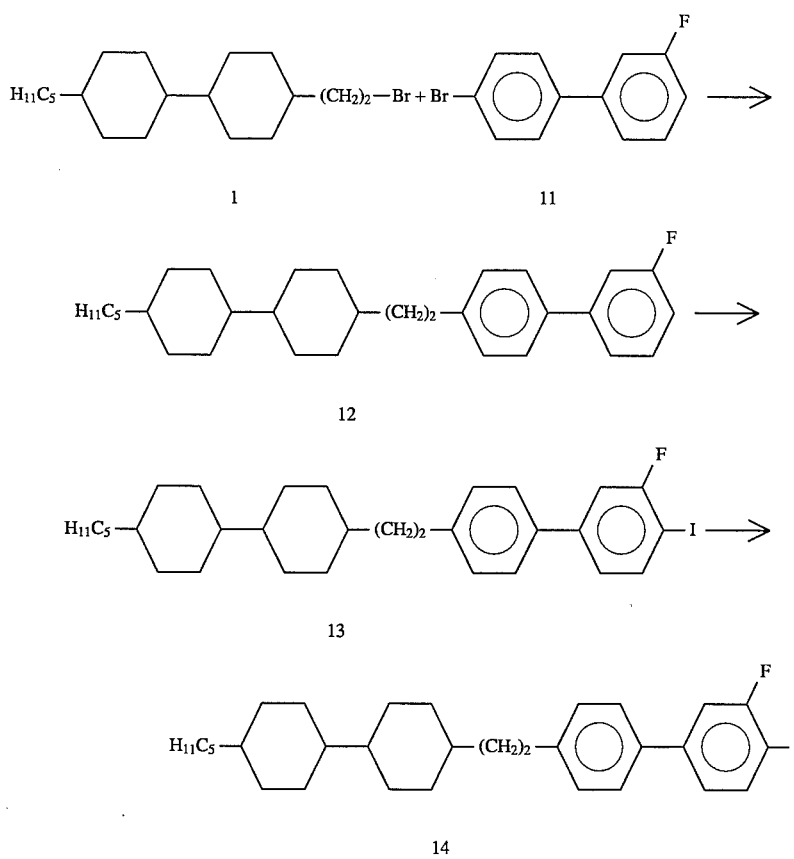

100 mol of 1 are converted into 12 by reaction with 11 analogously to the above example.

40 ml of n-BuLi are added dropwise at –100° C. to a mixture of 47 mmol of 12, 7.4 g of potassium tertiary-butoxide and 100 ml of THF, and the mixture is stirred at –100° C. for 1 hour. A solution of 15.9 g of iodine in 60 ml of THF is then added dropwise at –85° to –900 C. The mixture is stirred at –90° C. for a further 0.5 hours, warmed to –30° C., hydrolyzed using 30 ml of water and acidified using concentrated hydrochloric acid, and the excess iodine is reduced by adding sodium bisulfite solution. Customary work-up and recrystallization from hexane give 13. 38 mmol of 13 are converted into 14 by reaction with sodium trifluoroacetate. Chromatographic purification gives 14.

EXAMPLE 131

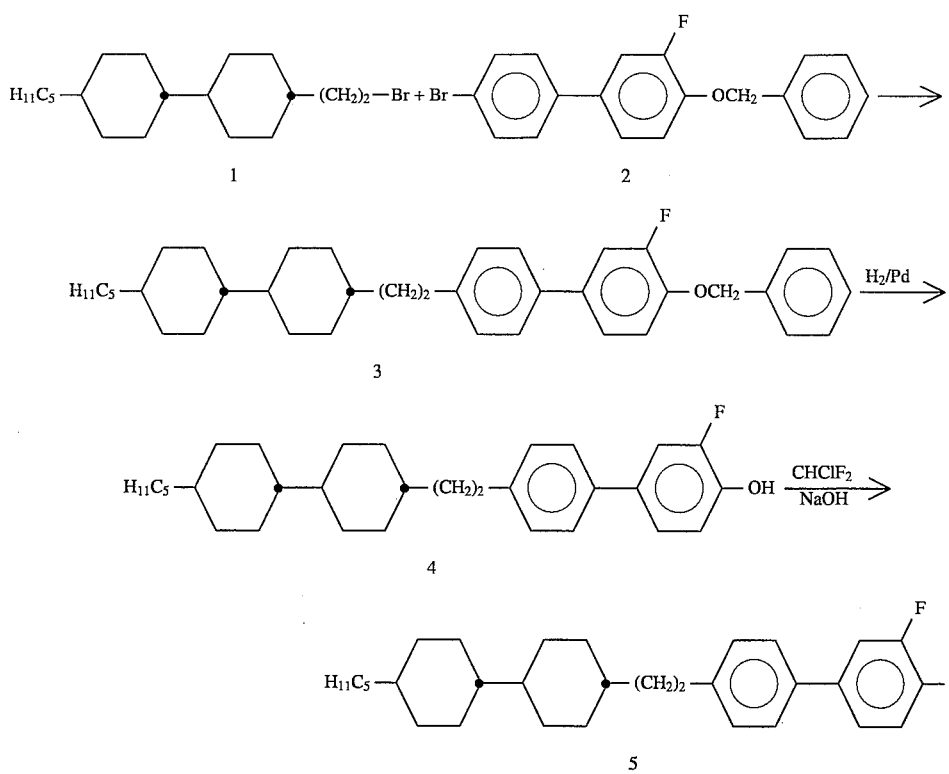

The compound 3 is obtained in accordance with the above synthesis scheme by a Pd(II)-catalyzed coupling reaction with 2 after conversion of 1 into the organozinc compound. Hydrogenolytic cleavage of the benzyl ether gives the phenol 4.

3.1 g of 32% sodium hydroxide solution and 0.5 g of tetrabutylammonium bisulfate are added to 0.01 mol of this phenol in THF, the mixture is warmed to 50° C., and chloride fluoromethane [sic] is passed-in with stirring until it condenses on a condenser cooled with dry ice. After cooling, the THF solution is decanted from the oily product which has precipitated, the solution is evaporated, and the 5 obtained is recrystallized from ethanol.

EXAMPLE 132

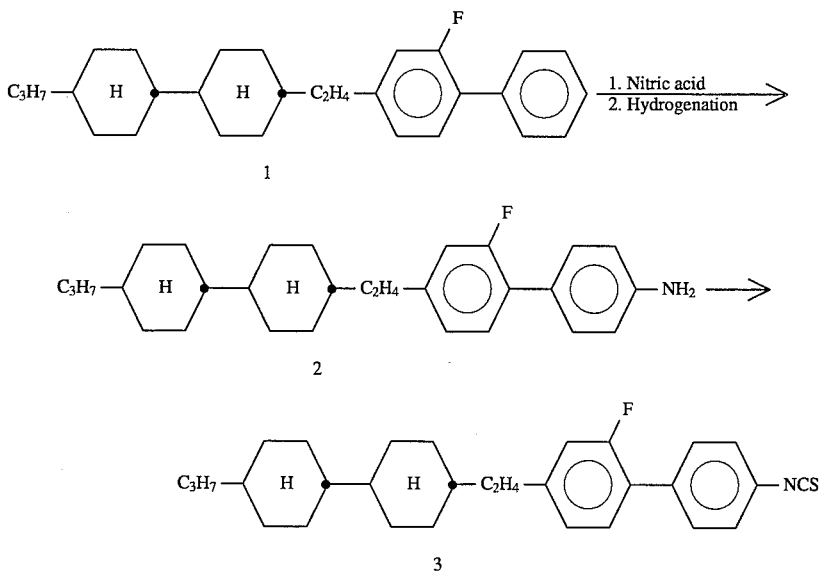

0.1 mol of thiophosgene is added dropwise to a solution of 0.1 mol of 2 (prepared by nitration of 1 and subsequent hydrogenation) and 15 ml of triethylamine in 100 ml of chloroform. The reaction mixture is then stirred overnight and then poured into 3N HCl. After the volatile constituents have been evaporated, pure 3 is obtained from the residue by recrystallization.

| Example A | |
|---|---|
| PCH-5F | 8% |
| PCH-6F | 6% |
| PCH-7F | 5% |
| CCP-20CF$_3$ | 6% |
| CCP-30CF$_3$ | 9% |
| CCP-40CF$_3$ | 6% |
| CCP-50CF$_3$ | 9% |
| BCH-3F.F | 9% |
| BCH-5F.F | 8% |
| ECCP-30CF$_3$ | 4% |
| ECCP-50CF$_3$ | 4% |
| CBC-33F | 2% |
| CBC-53F | 2% |
| CBC-55F | 2% |
| CCB-3.FOCF$_3$ | 10% |
| CCB-3.FF | 10% |
| Cl.P 92° C. | |
| V$_{th}$ 2.4 V | |

| Example B | |
|---|---|
| PCH-5F | 8% |
| PCH-6F | 6% |
| PCH-7F | 5% |
| CCP-20CF$_3$ | 6% |
| CCP-30CF$_3$ | 9% |
| CCP-40CF$_3$ | 6% |
| CCP-50CF$_3$ | 9% |
| BCH-3F.F | 9% |
| BCH-5F.F | 8% |
| ECCP-30CF$_3$ | 4% |
| ECCP-50CF$_3$ | 4% |
| CBC-33F | 2% |
| CBC-53F | 2% |
| CBC-55F | 2% |
| CCEB-3Cl.F | 10% |
| CCB-3Cl.F | 10% |
| cl.P 88° C. | |
| V$_{th}$ 2.2 V | |

We claim:

1. A benzene compound of the formula I

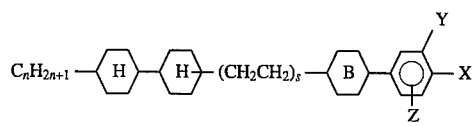

in which n is 1 to 10, B is 1,4-phenylene or 3-fluoro-1,4-phenylene, X is Cl, Y is hydrogen, Z is H or F, and s=0 or 1.

2. A benzene compound of the formula Ia

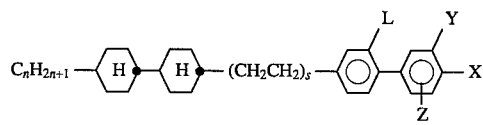

in which n is 1 to 7, s is 0 or 1, X is Cl, and Y, L and Z are each, independently of one another, H or F.

3. A benzene compound of the formula Iaa

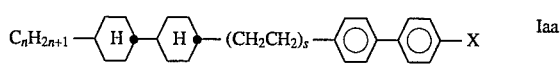

in which n is 1 to 7, s is 0 or 1 and X is Cl.

4. A benzene compound of the formula Iab

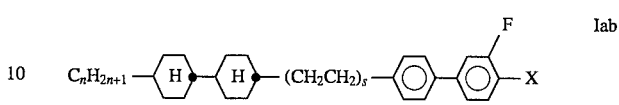

in which n is 1 to 7, s is 0 or 1 and X is Cl.

5. A benzene compound of the formula Iac

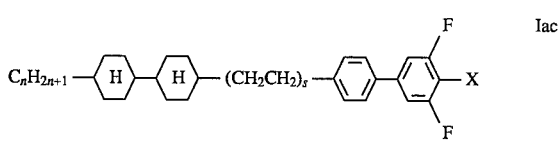

in which n is 1 to 7, s is 0 or 1 and X is Cl.

6. A benzene compound of the formula Iad

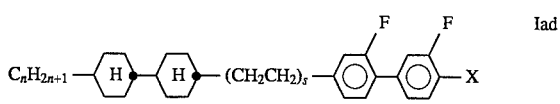

in which n is 1 to 7, s is 0 or 1 and X is Cl.

7. A benzene compound of the formula Iae

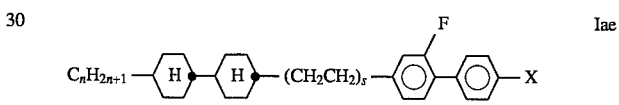

in which n is 1 to 7, s is 0 or 1 and X is Cl.

8. Liquid-crystalline medium for electro-optical displays, containing at least two liquid-crystalline components, wherein at least one component is a benzene, compound of the formula I according to claim 1.

9. Electro-optical display based on a liquid-crystal cell, wherein the liquid-crystal cell contains a medium according to claim 8.

10. A liquid-crystalline medium for electro-optical displays which comprises a benzene compound of claim 1.

11. A liquid-crystalline medium for electro-optical displays which comprises a benzene compound of claim 2.

12. A liquid-crystalline medium for electro-optical displays which comprises a benzene compound of claim 3.

13. A liquid-crystalline medium for electro-optical displays which comprises a benzene compound of claim 4.

14. A liquid-crystalline medium for electro-optical displays which comprises a benzene compound of claim 5.

15. A liquid-crystalline medium for electro-optical displays which comprises a benzene compound of claim 6.

16. A liquid-crystalline medium for electro-optical displays which comprises a benzene compound of claim 7.

* * * * *